United States Patent [19]

Tencza et al.

[11] Patent Number: 4,507,276

[45] Date of Patent: Mar. 26, 1985

[54] ANALGESIC CAPSULE

[75] Inventors: Thomas M. Tencza, Wallington; Mahesh K. Patell, Edison, both of N.J.

[73] Assignee: Bristol-Myers Company, New York, N.Y.

[21] Appl. No.: 410,167

[22] Filed: Aug. 20, 1982

[51] Int. Cl.³ .................. A61K 9/48; A61K 31/60
[52] U.S. Cl. ........................ 424/37; 514/162
[58] Field of Search .................. 424/19–22, 424/32, 33, 35, 37, 230, 233

[56] References Cited

U.S. PATENT DOCUMENTS

| | | | |
|---|---|---|---|
| 3,119,742 | 1/1964 | Hrimlich et al. | 167/82 |
| 3,155,590 | 11/1964 | Miller et al. | 424/35 |
| 3,341,416 | 9/1967 | Anderson et al. | 424/35 |
| 3,400,185 | 9/1968 | Kohnle et al. | 424/35 |
| 3,488,418 | 1/1970 | Holliday et al. | 424/35 |
| 3,524,910 | 8/1970 | Holliday et al. | 424/35 |
| 3,703,576 | 11/1972 | Kitajima et al. | 424/35 |
| 3,859,431 | 1/1975 | Newton et al. | 424/37 |
| 3,882,228 | 5/1975 | Boncey et al. | 424/35 |
| 3,887,700 | 6/1975 | Boncey et al. | 424/44 |
| 3,891,570 | 6/1975 | Fukushima et al. | 424/35 |
| 3,906,086 | 9/1975 | Guy et al. | 424/35 |
| 3,909,444 | 9/1975 | Anderson et al. | 424/32 |
| 4,049,803 | 9/1977 | Cotty et al. | 424/233 |
| 4,294,819 | 10/1981 | Tencza | 424/37 |
| 4,339,428 | 7/1982 | Tencza | 424/37 |

OTHER PUBLICATIONS

Lehmann et al, C.A. 97, #44253s, (1982), of Int. J. Pharm. Technol. Prod. Mfg., (1981), 2(4): 31–43.
Alpsten et al, C.A. 92, #28465d, (1980), of J. Pharm. Pharmacol., (1979), 31(7): 480–1.
Bogentoft et al, C.A. 90, #76495u, (1979), of Eur. J. Clin. Pharmacol. (1978), 14(5): 351–5.
Gurny et al, C.A. 88, #177119p, (1978), of Pharm. Acta Helv., (1977), 52(10): 247–251.
Kranz et al, C.A. 87, #122722d, (1977), of Pharm. Ind., (1977), 39(7): 712–715.
Ohno et al, C.A. 84, #111664y, (1976), of Ger. Offen, 2524813, 02 Jan. 1975.
Kitajima et al, C.A. 73, #78221d, (1970), of Ger. Offen, 2001726, 23 Jul. 1970.
Schoen et al, C.A. 74, #4375b, (1971), of Ger. Offen., 1,917,738, 08 Oct. 1970.
W. Kent Van Tyle, "Internal Analgesic Products", pp. 121–133, (1977), A. Ph. A., Handbook of Non-Prescripition Drugs, (fifth ed.), Wash., D.C.

*Primary Examiner*—Shep K. Rose
*Attorney, Agent, or Firm*—Gabriel P. Katona

[57] ABSTRACT

An analgesic capsule containing asprin and APAP. The aspirin is in the form of an enteric coated granule, and the APAP is present in powder form.

10 Claims, 1 Drawing Figure

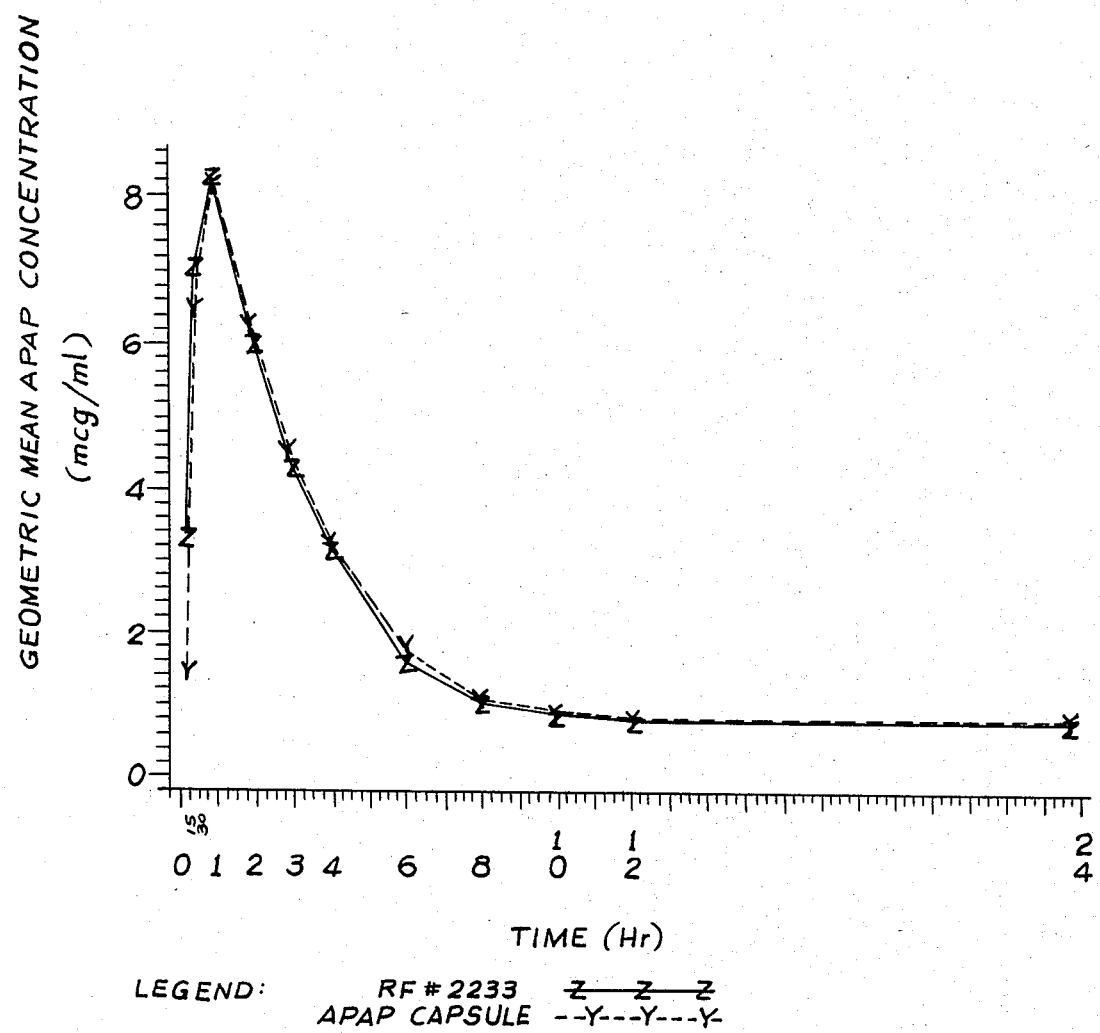

ANALGESIC CAPSULE

This invention relates to an analgesic product in capsule form containing a combination of aspirin and APAP (p-acetylaminophenol). More particularly, it concerns analgesic products of the aforementioned type in which the aspirin is present in said capsule in the form of an enteric coated granule.

Aspirin is still perhaps the most widely used over-the-counter analgesic. For some conditions, as is the case with arthritics, it still remains the drug of choice. However, difficulties are sometimes encountered in patients who take aspirin on a regular basis, particularly when it is taken in large doses. This can take the form of the so-called gastric intolerance which sometimes leads to gastric bleeding.

In an effort to eliminate this gastric intolerance, it has been suggested that aspirin tablets be provided with an enteric coating, i.e., a coating which resists digestion in the stomach but which enables the aspirin to be liberated in the intestines to be available for absorption into the bloodstream. The difficulty with this approach is that the time lapse between taking these tablets and attainment of a suitable blood level for aspirin is not acceptable.

It has also been suggested in the prior art to prepare a tablet which combines aspirin and APAP in a single tablet and in which the aspirin portion of the tablet is given an enteric coating. These tablets take the form of a central core tablet of aspirin which is provided with an enteric coating. Superimposed on this enteric coated aspirin core tablet is a layer of APAP designed for immediate release in the stomach. A product of this character is disclosed by Brennan, et al., in The British Journal of Clinical Practice, Vol. 24, No. 7, July 1970, pages 293-295.

To be effective, the aspirin in an aspirin-containing product must get into the bloodstream as aspirin or as some modification thereof referred to herein collectively as Salicylate. Moreover, the speed with which the Salicylate reaches its peak concentration in the blood after the administration of the product is believed to be an important feature in the speed of onset of the therapeutic effects that are attributable to aspirin. Similarly, the degree to which this speed to the peak concentration of Salicylate is reproducible on the administration of aspirin containing product (i.e., the lower the variability from subject to subject on the time to peak of Salicylate concentration in the blood), the more reliable is the aspirin containing product. On both of these counts, as will be pointed out in more detail below, enteric coated aspirin tablets leave much to be desired.

It has now been found that the time to peak of blood Salicylate concentration and the variability of this time to peak can be improved in an aspirin/APAP product, as compared with an enteric coated aspirin tablet, if the combination is such that the aspirin is present as enteric coated aspirin granules and the APAP is present as a powder and the combination is contained in a capsule, preferably in a hard gelatin capsule. This product provides a rapid onset of pain relief due to the presence of APAP powder in the capsules followed by further pain relief and any other therapeutic benefit due to the aspirin. The latter is accomplished without gastric intolerance because of the enteric coating on the aspirin granules.

It is, accordingly, an object of the present invention to provide an aspirin/APAP product in which the aspirin is present in the form of enteric coated aspirin granules and the APAP is present in the form of a powder, both of these materials being contained in a capsule.

It is a further object of this invention to provide an improved aspirin/APAP product of the aforesaid type designed to provide rapid onset of pain relief with APAP followed by further pain relief with aspirin, without gastric intolerance.

It is still a further object of this invention to provide a process for alleviating pain in a subject by administering an effective amount of the aforesaid aspirin/APAP product.

FIG. 1 is a graph plotting the geometric mean APAP concentration in mcg/ml of blood of the test subject over time after administration of formula RF #2233 and APAP Capsule, respectively.

Other and more detailed objects of this invention will be apparent from the following description and claims.

It has also been suggested in the prior art to enteric coat aspirin granules or pelletized aspirin particles. With respect to the latter, there is the further suggestion that these be dispensed in capsule form. These teachings are exemplified by the U.S. Patent to Kohnle, et al., No. 3,400,185 and a product disclosed to the trade in a seminar given by the Röhm Pharma Company of West Germany. However, there is no suggestion in the prior art that these enteric particles are to be incorporated in a capsule along with powdered APAP.

The enteric coated aspirin granules employed in the present invention may be prepared from aspirin granulations that are available to the trade or those that are manufactured by techniques well known to those skilled in this art. An example of the former is a product manufactured by Monsanto and marketed under the trade designation ASAGRAN 7017 or ASAGRAN 1640. The specifications for this product indicated that it assays at 99.5% to 100.5% for aspirin.

A typical procedure for preparing an aspirin granulation involves dry compaction of aspirin crystals with subsequent grinding or screening to desired size. An alternate method can be the traditional wet granulation method such as PVP in alcohol, Methocel in alcohol/water, various other resins such as Klucel in aqueous/alcoholic medium.

The granulated aspirin prepared as described above is provided with an enteric coating in accordance with the present invention. There are a variety of materials known in the prior art which are useful for this purpose. These generally can be characterized as polymers which resist solution in acidic pH, and rapidly dissolve at pH values of 6 and higher. Typical materials are CAP (cellulose acetate phthalate), ethyl cellulose, hyroxypropyl methylcellulose phthalate-Grade HP55, and Aquacoat (FMC Corp.).

The enteric coating can be applied to the aspirin granulation by any of a variety of procedures. A typical procedure involves the use of a fluid bed granulator to apply the enteric coating to aspirin granules suspended in a fluidized bed. An alternate procedure is to use a spray assembly with a conventional coating pan.

The enteric coating materials of choice are polymeric acrylic or methacrylic acids or their corresponding lower alkyl esters, e.g., methylmethacrylate. These are applied to the aspirin granulation in the form of a 30% aqueous dispersion with application of 7 to 12% of the polymer by dry weight. Of special use in this regard is a product marketed by the Röhm Pharma Company of West Germany under the trade designation EUDRAGIT L-30D. This is a 30% aqueous dispersion of an anionic polymer synthesized from methacrylic acid and methacrylic acid methyl ester.

The capsules of the present invention may contain varying amounts of aspirin and APAP in various proportions, depending on the subject or condition treated. For example, the aspirin and APAP may be present in 1:1, 1:2, 1:3, 2:1 or 3:1 ratios. In general, the capsules may contain from about 80 to 650 mgs. of therapeutically active ingredients.

The quantity of enteric coated granulated aspirin and the quantity of APAP that will be contained in the capsules of the present invention may each vary depending upon the subject or condition treated, as well as the number of capsules that the therapeutic regimen will call for. In general, a dose amount of therapeutically active ingredients is from about 80 mgs. to about 1300 mgs., preferably from about 500 mgs. to about 1300 mgs., the dose amount of enteric coated granulated aspirin being from about 40 mgs. to about 650 mgs., preferably from about 500 mgs. to about 650 mgs., and the dose amount of APAP being similarly from about 40 mgs. to about 650 mgs., preferably from about 500 mgs. to about 650 mgs. Dose amounts of therapeutically active ingredients of less than 650 mgs. may be contained in a single capsule of the present invention, although preferably the aforesaid dose amounts of more than 160 mgs. are distributed over two or more capsules which are intended to be taken at the same time. In the usual case, the dose of therapeutically active ingredients will be contained in two capsules of the present invention, each capsule containing from about 40 mgs. to about 325 mgs. of enteric coated granulated aspirin, preferably from about 250 mgs. to about 325 mgs., and from about 40 mgs. to about 325 mgs. of APAP, preferably from about 250 mgs. to about 325 mgs., which capsules are intended to be taken at the same time.

In addition to the enteric coated aspirin and the APAP, the capsule may also contain other therapeutically active ingredients or adjuvants. By way of examples of the other active ingredients, mention may be made of magnesium salicylate, salicylamide, caffeine, sodium salicylate, chlorpheniramine maleate, pseudophedrine HCl, phenylpropanolamine HCl, dextromethorphan HBr, and diphenhydramine hydrochloride. As to the adjuvants that may be added, these are exemplified by such things as modified starch 1500, regular corn starch as disintegrants, flow agents such as magnesium stearate, talc, silicone fluid, zinc stearate and surfactants such as Tween 80, Aerosol OT and sodium lauryl sulfate.

The following Examples are given to further illustrate the present invention. It is to be understood, however, that this invention is not limited thereto.

The following terms when used in the Examples and elsewhere in this specification will have the meanings ascribed to them below.

EUDRAGIT L-30D: is a copolymer, anionic in character, based on polymethacrylic acid and polymethacrylic acid esters with a ratio of free carboxyl groups to ester groups of about 1:1.

Medical Antifoam AF Emulsion: 30% simethicone (polydimethylsiloxane and silicone dioxide 14% stearate emulsifiers; 0.075% sorbic acid and water to 100%).

EXAMPLE 1

Formula RF #2233

| Dosage Unit Amt. mg./cap. | Item No. | Ingredients | % Each Part | % Total Weight |
|---|---|---|---|---|
| | | Part I Enteric Coated Aspirin Granules | | |
| 326.634 | 1 | Aspirin - as ASAGRAN 7017 granules (Monsanto weight taken based on 99.5% Assay spec.) | 90.868 | 47.382 |
| 24.497 | *2 | EUDRAGIT L-30D (30%/w applied as an aqueous dispersion) Rohm Pharma GmbH Germany | 6.815 | 3.554 |
| 5.715 | 3 | Talcum Powder | 1.590 | 0.829 |
| 2.452 | 4 | Triethyl citrate | 0.682 | 0.356 |
| 0.162 | 5 | Medical antifoam AF emulsion (Dow Chemical) | 0.045 | 0.023 |
| — | **6 | Water, deionized and distilled | — | |
| (359.460) | | | 100.000 | |
| | | Part II Final Blend for Encapsulation | | |
| 359.460 | ***7 | Part I above | 52.144 | — |
| 325.000 | 8 | Acetaminophen | 47.145 | 47.145 |
| 2.500 | 9 | Dimethylpolysiloxane Fluid 360 Medical Type 350 centistokes | 0.363 | 0.363 |
| 1.000 | 10 | Polyoxyethylene(20) sorbitan monooleate | 0.145 | 0.145 |
| 1.400 | 11 | Sodium lauryl sulfate | 0.203 | 0.203 |
| 689.360 | | | | |
| 10.64 | ***12 | StaRx 1500 Starch LM (Q.S. to capsule fill weight) | | |
| 700.00 | | | | |

*Should be stored at temp. between 5–20° C.
**Evaporates during coating process
***Weight of item 7 in Part II varies ±3% depending on the aspirin content of the coated granules. Capsule fill weight (net) to be q.s. with item 12

Procedure:

Part I—Enteric Coated Aspirin Product

Aspirin (Item 1) is enteric coated using solution made from Items 2, 3, 4, 5 and 6 as described below.
Preparation of the Coating Solution:
1. Talcum Powder (Item 3) is suspended in water with high shear. Then add Items 4 and 5, mix well.
2. Slowly add Item 2, mix very gently (higher shear causes coagulation of Eudragit, which cannot be redispersed).

Coating Process:
1. Item 1 is placed in fluid bed spray granulator/dryer (screen through #8 mesh if lumpy).
2. Granules are preheated to about 50° C. exhaust temperature (approx. 2 min.).
3. Coating solution is sprayed at about 150 ml/min. with exhaust air temp. at 40°–45° C. with nozzle size 1.8 mm. After completion of the coating, the granules are dried for 15 min. with the inlet temp. reduced to 45° C.
4. These coated granules are dried overnight (at least 24 hours) at about 100° F. on trays in oven with air on.

Part II—Final Blend for Encapsulation

1. Place Item 7 in twin shell blender; add Item 11; mix well.
2. Add Item 8 & item 12 to the blender (screen if lumpy) and mix well.

3. Mix Items 9 and 10 together; add to above blend and mix well.

Capsule Fill on H&K Machine

Place above Part II granules in the hopper of the capsule filling machine and fill into capsules to specifications below.

Capsule size #0
Wt. 700 mg. (net)
Aspirin 325 mg. ±10%
APAP 325 mg. ±10%

EXAMPLE II

Formula RF #2258

The following formulation for Enteric Coated Aspirin Granules would be suitable for use as Item 7 of Example I above in the amount stated therein:

| Item | Part I Enteric Coated Aspirin Granules | % Total Solids |
|---|---|---|

| No. | Ingredients | (Part I) |
|---|---|---|
| 1 | Aspirin - as ASAGRAN 1640 granules (Monsanto) | 91.213 |
| *2 | EUDRAGIT L-30D (30%/w applied as an aqueous dispersion) Rohm Pharm GmbH Germany | 6.841 |
| 3 | Talcum Powder | 1.216 |
| 4 | Triethyl citrate | 0.684 |
| 5 | Medical Antifoam AF emulsion (Dow Chemical) | 0.046 |
| **6 | Water, deionized and distilled | — |
| | | 100.00 |

*Should be stored at temp. between 5-20° C.
**Evaporates during coating process.

Procedure: Same as for Example I.

A bioavailability study was conducted to evaluate the bioavailability of the aspirin and APAP from a typical product of the present invention (Product of Example 1 RF #2233) and to compare them with their availability from a commercial powdered APAP capsule product (APAP Capsule), a commercial enteric coated aspirin tablet (Enteric ASA Tablet) and a commercial aspirin tablet (ASA Tablet). The APAP absorption from said typical product was compared with the APAP absorption from the APAP Capsule; whereas, the aspirin absorption was compared with the aspirin absorption from the Enteric ASA Tablet and the ASA Tablet. The levels of the active ingredients in each product tested is given below:

(a) RF #2233: 5 grains aspirin & 5 grains APAP
(b) Enteric ASA Tablet: 5 grains aspirin
(c) ASA Tablet: 5 grains aspirin
(d) APAP Capsule: 5 grains APAP Method:

The study involved 23 adults; 11 males and 12 females. Blood withdrawals were taken at 0, 15, and 30 minutes and 1, 2, 3, 4, 6, 8, 10, 12, and 24 hours following scheduled 2-tablet or 2-capsule dosing. Each subject tested the four medications in one of four different orders. The blood levels of APAP or Salicylate were determined using standard technique.

The comparison of the bioavailability for APAP from RF #2233 of this invention as compared with APAP Capsules is summarized in the graph of FIG. 1. The curve for RF #2233 is essentially superimposed on the curve for the APAP Capsules and indicates that the APAP of formula RF #2233 is immediately available to provide its therapeutic effect in accordance with the rationale of the products of the present invention.

Table 1 below summarizes the mean time to peak concentration for Salicylate for each of the products tested. This is a measure of the time it takes after the ingestion of the respective products by the subject for his blood level for Salicylate to reach its maximum. The shorter this time period, the quicker it would be expected for the Salicylate to exert its therapeutic effect.

TABLE 1

| Product | N | MIN. | MAX. | RANGE | VAR. | TIME | RANK SUM |
|---|---|---|---|---|---|---|---|
| 1 ASA Tablet | 23 | 0.5 | 4 | 3.5 | 0.882 | 1.8 | 23 |
| 2 RF #2233 | 23 | 4.0 | 6 | 2.0 | 0.949 | 5.3 | 48 |
| 3 Enteric ASA Tablet | 23 | 6.0 | 10 | 4.0 | 2.719 | 7.9 | 67 |

| CHI SQ | P VALUE |
|---|---|
| 42.3 | .000 |

The Table discloses that as would be expected the time to peak for uncoated aspirin is fastest. This is due to the fact that the uncoated aspirin is available for almost immediate absorption from the stomach. However, as indicated above, a product of this character can cause a degree of gastric intolerance in some subjects.

A comparison of products 2 and 3 of Table 1, however, will show that the time to peak for Salicylate for the product of the present invention (product 2) is significantly faster than for the enteric coated aspirin tablet (product 3), i.e., 5.3 hours as compared with 7.9 hours. Furthermore, the variability for the time to peak of blood Salicylate from subject to subject is significantly smaller for the product of this invention (2) as compared with the enteric coated aspirin tablet (3), i.e., 0.949 as compared with 2.719. These measurements indicate that the therapeutic activity for the aspirin in the present product should come on more rapidly than the aspirin from the enteric coated aspirin tablet. Moreover, it further shows that this rapid activity should be more dependable and reproducible from subject to subject.

What is claimed is:

1. As an article of manufacture, a therapeutically effective dose of aspirin and APAP in capsule form; said dose comprising a therapeutically effective amount of enteric coated aspirin granules and APAP in powdered form; said dose being designed to provide APAP available for immediate absorption into the bloodstream from the stomach and aspirin and aspirin for delayed absorption into the bloodstream from the intestines whereby the danger of gastric intolerance due to the presence of aspirin in the stomach is significantly diminished or eliminated.

2. An article of manufacture according to claim 1 in which the aspirin is present in said dose in the range of from 80 mgs. to about 650 mgs. and said APAP is present in the range of from about 80 mgs to about 650 mgs.

3. An article of manufacture according to claim 1 in which the aspirin is present in said dose in the range of from 250 mgs. to 325 mgs. and said APAP is present in the range of from 250 mgs. to 325 mgs.

4. An article of manufacture according to claim 2 or 3 in which said dose takes the form of two capsules.

5. An article of manufacture according to claim 2 or 3 in which said dose takes the form of two capsules, each capsule containing one-half of the aspirin and one-half of the APAP contained in said dose.

6. An article of manufacture according to claim 1 in which said enteric coating material is a copolymer, anionic in character, based on polymethacrylic acid and polymethacrylic acid esters with a ratio of free carboxyl groups to ester groups of about 1:1.

7. As an article of manufacture, a hard gelatin capsule containing from about 250 mgs. to about 325 mgs. of enteric coated aspirin granules and from about 250 mgs. to about 325 mgs. of powdered APAP.

8. An article of manufacture according to claim 7 in which said hard gelatin capsule contains from about 250 mgs. of enteric coated aspirin granules and from about 250 mgs. of powdered APAP.

9. An article of manufacture according to claim 8 containing about 325 mgs. of enteric coated aspirin granules and 325 mgs. of powdered APAP.

10. A process for inducing analgesia in a subject which comprises administering to said subject the effective dose of aspirin and APAP in the form defined in claims 1, 2, 3, 4, 5, 6, 7, 8, or 9.

* * * * *